(12) United States Patent
Garde et al.

(10) Patent No.: US 9,216,387 B2
(45) Date of Patent: *Dec. 22, 2015

(54) METHOD AND SYSTEM FOR IMPROVED PROCESS PARAMETER CONTROL OF A LIQUID COMPOSITION IN A REVERSE ELECTRO-ENHANCED DIALYSIS (REED) SYSTEM

(71) Applicant: CARLSBERG A/S, Koebenhavn V (DK)

(72) Inventors: Arvid Garde, Hilleroed (DK); Jens-Ulrik Rype, Gentofte (DK)

(73) Assignee: CARLSBERG A/S, Kobenhavn V (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/596,958

(22) Filed: Jan. 14, 2015

(65) Prior Publication Data

US 2015/0182915 A1 Jul. 2, 2015

Related U.S. Application Data

(63) Continuation of application No. 13/062,806, filed as application No. PCT/EP2009/006438 on Sep. 4, 2009, now Pat. No. 8,961,769.

(60) Provisional application No. 61/095,123, filed on Sep. 8, 2008.

(30) Foreign Application Priority Data

Sep. 8, 2008 (EP) ..................................... 08163856

(51) Int. Cl.
*B01D 61/44* (2006.01)
*B01D 61/50* (2006.01)
*B01D 61/42* (2006.01)
*B01D 61/52* (2006.01)
*B01D 61/54* (2006.01)
*C12N 1/16* (2006.01)
*C12N 1/20* (2006.01)

(52) U.S. Cl.
CPC .............. *B01D 61/50* (2013.01); *B01D 61/422* (2013.01); *B01D 61/44* (2013.01); *B01D 61/52* (2013.01); *B01D 61/54* (2013.01); *C12N 1/16* (2013.01); *C12N 1/20* (2013.01); *B01D 2311/2688* (2013.01); *B01D 2317/02* (2013.01); *B01D 2317/04* (2013.01); *B01D 2317/06* (2013.01); *B01D 2317/08* (2013.01)

(58) Field of Classification Search
CPC ...... B01D 61/50; B01D 61/54; B01D 61/422; B01D 61/44; B01D 61/52; B01D 2311/2688; B01D 2317/04; B01D 2317/06; B01D 2317/02; B01D 2317/08; C12N 1/20; C12N 1/16
USPC .......................... 204/523, 525, 528, 530, 630
See application file for complete search history.

(56) References Cited

U.S. PATENT DOCUMENTS 8,961,769 B2 * 2/2015 Garde et al. .................. 204/523

* cited by examiner

*Primary Examiner* — Arun S Phasge
(74) *Attorney, Agent, or Firm* — Novak Druce Connolly Bove + Quigg LLP

(57) ABSTRACT

A method and a system for process parameter control of a liquid composition in a reverse electro-enhanced dialysis (REED) system comprising at least two Reverse Electro-Enhanced Dialysis (REED) membrane stacks, wherein the direction of the electric field within any one membrane stack is reversed at asynchronical intervals of time relative to the current reversals for any other membrane stack.

20 Claims, 1 Drawing Sheet

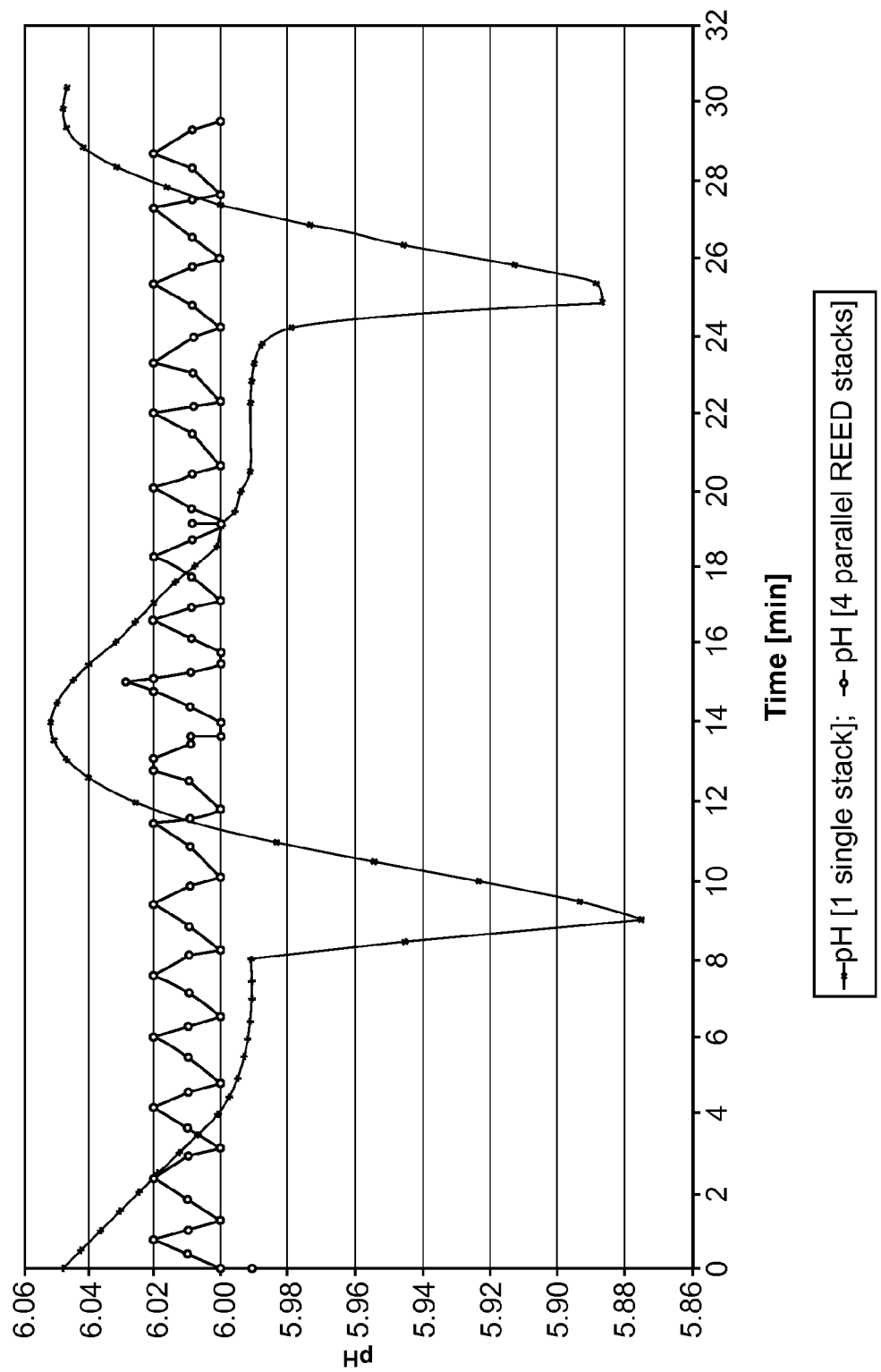

METHOD AND SYSTEM FOR IMPROVED PROCESS PARAMETER CONTROL OF A LIQUID COMPOSITION IN A REVERSE ELECTRO-ENHANCED DIALYSIS (REED) SYSTEM

CROSS REFERENCE TO RELATED APPLICATIONS

This application is a continuation application of U.S. application Ser. No. 13/062,806, filed May 25, 2011, entitled "METHOD AND SYSTEM FOR IMPROVED PROCESS PARAMETER CONTROL OF A LIQUID COMPOSITION IN A REVERSE ELECTRO-ENHANCED DIALYSIS (REED) SYSTEM, which is a §371 national phase entry of International Application No. PCT/EP2009/006438, filed Sep. 4, 2009, which claims priority to European Application No. 08163856.1, filed Sep. 8, 2008, and U.S. Provisional Patent Application No. 61/095,123, filed Sep. 8, 2008, the entire contents of which are incorporated herein by reference.

FIELD OF THE INVENTION

The present invention relates to a method and a system for improved process parameter control of a liquid composition in a reverse electro-enhanced dialysis (REED) system comprising at least two Reverse Electro-Enhanced Dialysis (REED) membrane stacks, wherein the direction of the electric field within any one membrane stack is reversed at asynchronical intervals of time relative to the reversal of the electric field for any other membrane stack. Furthermore, the present invention relates to a method and a system for improved parameter control of a liquid composition in a reverse electro-enhanced dialysis (REED) system, wherein the parameter control mechanism is induced through a combination of electrical DC current regulation and regulation of dialysate solution composition.

BACKGROUND OF THE INVENTION

Controlling the pH, conductivity and/or the level of target ions of a liquid composition is an important industrial process used within such broad technical fields as metal refining and purification of organic substances from a fermented liquid.

A number of processes have been introduced in order to control the level of target ions or pH of a liquid composition. Among said processes are micro- and ultrafiltration processes, ion-exchange processes and electrodialysis processes.

E.g. bioreactors are used extensively in the industry for production of a wide range of organic chemicals, pharmaceutical proteins, amino acids, starter cultures, biofuels etc., or for biodegradation purposes. Most often, the bioreactor contains microorganisms that require a certain pH level to sustain optimal functionality.

Standard means for pH regulation in bioreactors includes titration of alkaline or acidic neutraliser directly into the bioreactor, to neutralize acidic or alkaline metabolites produced by the microorganisms. However, salts of these metabolites often inhibit growth when reaching a certain concentration.

The build-up of some salts and metabolites, such as inhibitors for biological reactions, sets a limit to the productivity of a bioreactor in normal batch operations. Possible solutions to minimize inhibition include perfusion systems, where fermentation broth with inhibitors is continuously extracted through a filter process (e.g. ultra- or microfiltration), while retaining the microorganisms and adding fresh substrate solution to the fermenter. In perfusion systems, it is still necessary to regulate bioreactor pH through titration of neutralizer and valuable substrate components are lost with the permeate.

The use of ion-exchange membranes, as utilized in electrodialysis and the so-called Donnan Dialysis processes, allows for a more selective extraction of small charged species compared to membranes typically used in ultra- and microfiltration. However, conventional electrodialysis suffers from membrane fouling when combined directly with bioreactors and neutralizer titration is still necessary for pH control.

EP patent 1 237 823 discloses an apparatus and a method for transferring ionic species from a first liquid to a second liquid in an electro-enhanced dialysis cell comprising either cation exchange membranes or anion exchange membranes.

U.S. Pat. No. 5,114,554 discloses a process for removing acid from a cathodic electrocoating bath in which electroconductive substrates are being coated with cationic resins, at least a portion of the coating bath being subjected to an ultrafiltration, and at least a portion of the ultrafiltrate being subjected to a specific electrodialysis treatment in a direct current operated electrodialysis cell comprising anion exchange membranes.

SUMMARY OF THE INVENTION

There is a need for a method and a system for improved process parameter control of a liquid composition, which process allows control of pH, the concentration of the target ion and/or conductivity of said liquid composition and reduction of concentration fluctuations caused by reversals of the electric field ("current reversals"). Especially fluctuations in pH can have negative effect on microbial systems and hence must be avoided. Furthermore, some biological systems, e.g. protein expression systems, are sensitive to fluctuations in target ion concentration.

Thus in a first aspect the present invention relates to a method for process parameter control of a liquid composition comprising at least one step of passing said liquid through a first Reverse Electro-Enhanced Dialysis (REED) membrane stack and a second REED membrane stack, each stack having:
  i) at least two ion-exchange membranes defining a first chamber for a first liquid there between;
  ii) at least two further chambers for a second liquid, each further chamber being located adjacent to the at least one first chamber;
  iii) a set of end membranes;
  iv) means for applying an electric field over each membrane stack by means of at least two electrodes;
  v) means for reversing the direction of the electric field within said membrane stacks;
wherein the direction of the electric field within said first membrane stack is reversed at asynchronical intervals of time relative to the reversal of the electric field within said second membrane stack.

A second aspect of the invention is a system for process parameter control of a liquid composition, said system comprising at least a first Reverse Electro-Enhanced Dialysis (REED) membrane stack and a second REED membrane stack, each stack having:
  i) at least two ion-exchange membranes defining a first chamber for a first liquid there between;
  ii) at least two further chambers for a second liquid, each further chamber being located adjacent to the at least one first chamber;
  iii) a set of end membranes; and iv) means for applying an electric field over each membrane stack by means of at least two electrodes;

v) means for reversing the direction of the electric field within any one membrane stack.

A third aspect of the invention is the use of a system according to the invention for process parameter control of a liquid composition.

Other aspects of the invention will become apparent to the person skilled in the art from the following detailed description and examples.

DEFINITIONS

In the context of this invention the term "target ion(s)" is meant to encompass both unwanted ions, e.g. inhibitors in a fermentation process, and ions constituting a desired product being removed from the liquid composition. As a non-limiting example of a target ion may be mentioned the lactate ion. Lactic acid is a known inhibitor for Lactic Acid Bacteria (LAB) cultures, and thus, for bioreactors with live LAB cultures, lactate could be a target ion for the REED process. The term "target ions" does not encompass hydrogen ions.

In the context of this invention the term "Reverse Electro-Enhanced Dialysis" or "REED" covers both AX-REED and CX-REED.

In the context of this invention the term "AX-REED" means a REED setup where Anion-exchange membranes are used as barrier between feed solution and dialysate and exchange of anions between the two liquids is facilitated.

In the context of this invention the term "CX-REED" means a REED setup where Cation-exchange membranes are used as barrier between feed solution and dialysate and exchange of cations between the two liquids is facilitated.

In the context of this invention the term "reversal of the electric field" or "current reversal" means the changing of polarity of the REED electrodes, resulting in a reversal of the direction of the electrical DC current, which facilitates the migration of ions through the ion-exchange membranes.

In the context of this invention the term "current reversal interval" means the time between each current reversal for any given REED stack.

In the context of this invention the term "dispersal interval" means the time between a current reversal for a first REED stack and the consecutive current reversal of a second or further REED stack in REED systems with multiple REED stacks with asynchronical current reversal intervals.

In the context of this invention the term "stack" means a unit of a REED system comprising one or more repeating sets of a combination of at least two ion-exchange membranes, a set of end membranes and at least two electrodes surrounding said membranes.

In the context of this invention the term "multiple REED membrane stacks" means two or more stacks of membranes and spacers, each stack placed between a pair of electrodes.

In the context of this invention the term "control" or "controlling" means the ability, manually or automatically to adjust the desired parameter, e.g. pH, concentration of target ions, conductivity using REED.

BRIEF DESCRIPTION OF THE DRAWINGS

The invention is disclosed with reference to the drawings, wherein

FIG. 1 shows two pH curves for similar bioreactor systems, a reference system controlled by a single REED stack and a system according to the invention controlled by 4 parallel REED stacks.

DETAILED DESCRIPTION OF THE INVENTION

REED Principle

The Reverse Electro-Enhanced Dialysis (REED) process utilizes ion-exchange membranes in a plate-and-frame membrane setup similar to the so-called Donnan Dialysis setup, the latter utilizing diffusion caused by a difference in chemicals potentials as the driving force. However, in the REED process the exchange of ions is boosted and regulated by an electrical DC current across the membrane setup. The REED process is intended for use on process solutions entailing components too large to penetrate the membranes (e.g. proteins), which tend to collect on the surface of ion-exchange membranes; this effect is known as membrane fouling. By utilizing the REED process's symmetrical setup, the direction of the electrical current can be reversed at intervals without significant interference in the separation process.

Typically, a process solution (feed solution) flows through a REED system, where either negatively charged ions (anions) are exchanged for other anions, thus named an Anion Exchange REED setup (AX-REED), or positively charged ions (cations) are exchanged for other cations in a Cation Exchange REED setup (CX-REED). A dialysate solution carries the ions, which are exchanged for the ions in the feed solution. In a plate-and-frame setup, several membranes are stacked, separated by flow spacers facilitating alternately the feed and the dialysate solutions, respectively.

During the separation, the two membranes surrounding each feed spacer compartment either facilitates the transport of ions out of the feed solution or into the feed solution from the dialysate. The polarity of said at least two electrodes is changed at intervals.

Each reversal of the direction of the electric field/electrical current results in a short-term reestablishment of the affected ions' polarization profiles at the surface and inside the membranes, as the two membranes surrounding each feed compartment exchanges functions. This causes a short-term reversal of the separation process as the ions previously being removed are pushed back into the feed solution until the membrane profiles are re-established. It is advantageous to keep the intervals between current reversals within any one REED stack as long as allowed by the build-up of fouling, as each reversal introduces a short separation pause and introduces minor process instability.

In an embodiment of the invention the process parameters to be controlled are selected among pH, concentration of target ions and/or conductivity of said liquid composition. For process streams, where the REED system is used for desalting of ions (e.g. inorganic salts, amino acids, organic acids, ammonium ion) or regulation of salinity, the conductivity is typically the primary control process parameter. Furthermore, for regulation of target ion concentration, which for some species or systems can be difficult or impossible to measure online, conductivity measurement can be used as a process control parameter.

In an embodiment of the invention said liquid composition is passed through at least one further REED membrane stack.

Electro-membrane processes e.g. electrodialysis and REED utilizes a plate-and-frame membrane setup. The plate-and-frame membrane setup allows for easy and compact stacking of membrane area, as membrane sheets are stacked (commonly separated by membrane spacers) on top of each other until sufficient membrane separation area is achieved. For feasible handling, operational, and maintenance purposes, plate-and-frame systems are typically operated in several separate, practically sized membrane stacks, each with its own set of flow connections and electrodes, but with the same separation function. These stacks are operated together in parallel or serial or some combination thereof as part of the same separation system. For compact systems, it is advantageous to keep the number of separate plate-and-frame stacks low, each stack having as much membrane area as technically feasible. But for optimized process control of REED systems, where each separate stack introduces a fluctuation in overall process parameter control, it is advantageous to operate with multiple REED stacks, or multiple REED stack sections, when more than one set of electrodes are used. The number of stacks may thus vary from 2 to several hundreds depending on the process in question, but are typically in the range 2-50, more typically 4-20 stacks.

The REED process may be used for extracting inhibitors like organic acid ions from bioreactors/live fermentation processes to improve productivity and longevity of cell growth (continuous fermentation) and/or to regulate metabolite production (e.g. recombinant protein). The REED process may e.g. be used for pH control in biological, bioconversion, or catalytic systems, where a small acidic or alkaline component is continuously produced (e.g. lactate, acetate, ammonia, nitrate). By exchanging produced organic acid ions for hydroxide ions from an alkaline dialysate solution, which then neutralize the accompanying hydrogen ions, the overall result is a constant pH and significantly reduced accumulation of organic acid level. The case is similar for alkaline forming systems, where the alkaline ions are exchanged for hydrogen ions from an acidic dialysate, which in turn neutralize the hydroxide ions in the feed solution. In biological systems where the produced acids or alkalis act as growth inhibitors, the REED system's pH control is preferable to the standard pH titration control directly into the biological system, which only maintains pH level, but in itself is unable to suppress the build-up of neutralized acidic or alkaline metabolites.

In an embodiment of the invention said at least first and second REED stacks are operated in parallel. Such set-up minimizes e.g. the impact on microorganisms in a bioreactor as the holding time outside the bioreactor as well as the pH deviation from the set point is reduced compared to operation in series.

In another embodiment of the invention said at least first and second REED stacks are operated in series or cascade. Such set-up allows for higher removal of ions per pass and is better suited for continuous downstream operations.

The previously described short-term effect following each current reversal impacts the REED system's pH control by introducing a short-term negative effect until the membranes' ion profiles are re-established. In the case of AX-REED, acidic ions are extracted through one anion-exchange membrane in each feed compartment, while hydroxide ions enter through the opposite anion-exchange membrane. When the direction of the electrical current is reversed, the extracted acidic ions inside the first mentioned membrane is pushed back into the feed solution, before hydroxide ions starts entering the feed solution. Thus, in the short time period until the hydroxide profile is re-established through the membrane, which was previously used to extract acidic ions, no pH control is observed. The length of the time phase after each current reversal until pH control is regenerated depends on various process conditions and membrane properties; typically, it takes between 10-90 seconds before the process is again operating at optimal process parameter control. This is registered as a sudden change in the process parameter e.g. pH, which must then be regulated back to the desired setpoint. In order to spread out the instability effects and reduce the overall impact of current reversals with more than one membrane stack, the current reversals on each separate stack are performed asynchronically. Even though the current reversal intervals for each stack are typically of similar length, the timing of the reversals are dispersed for best process stability effect.

In an embodiment of the invention the direction of the electric field within any first membrane stack is reversed at substantially regular dispersal intervals relative to the reversals for any second or further membrane stack.

The interval length between current reversals for a stack is typically chosen with regard to the build-up of membrane fouling. Typically, said intervals within any one REED stack may be in the range 5-6000 seconds, preferably 8-3000 seconds, more preferably 10-2000 seconds and even more preferably 100-1500 seconds. In a system according to the prior art with a single REED stack, a connected bioreactor, which is controlled by the REED system, will experience the full impact of pH fluctuations at every reversal, and hence at the end of each current reversal interval. However, for multiple stacks with substantially regular dispersal intervals between said current reversals, the fluctuations experienced will be reduced.

In another embodiment of the invention the direction of the electric field within any first membrane stack is reversed at dispersal intervals of substantially even length relative to the reversals for any second or further membrane stack in order to maximise the time between a current reversal of any first REED stack and any second or further REED stack in the same process. With the same dispersal interval length between current reversals, i.e. where these reversals are dispersed evenly the connected bioreactor will experience a reduced impact, but much more often. Thus in a system with e.g. four parallel REED stacks with 12 min. current reversal intervals, a connected, process parameter-controlled bioreactor would experience a fluctuation in the process parameter every 3 min., although from only ¼ of the full REED system and with ¼ or less of the deviation from control setpoint, compared to a system operating at equal current reversal interval length (12 min.), but with a single REED stack (or four stacks with synchronised current reversal intervals).

In an embodiment of the invention the intensity of the applied electric field is adjusted in response to the pH, target ion concentration or conductivity of said liquid composition. By increasing the intensity of the electric field, the ion exchange increases in the REED system, and vice versa. Online, semi-online (e.g. time-delayed) or secondary (e.g. using online conductivity or turbidity measurements for estimating target ion concentration) measurements of the process parameters being regulated are input in a control regulation mechanism e.g. PID-control software, which in turn regulates the output of the power supplies to the REED electrodes.

A REED system is typically (but not always) operated to control and regulate one specific process parameter of the process to which it is connected. The control regulation is carried out by controlling the ion exchange taking place inside the REED system. Process parameters, which are controlled in this manner include, but are not limited to; pH, conductivity, and target ion concentration. Combining separate REED systems to the same process (e.g. AX-REED and CX-REED) allows for control of multiple process parameters, wherein each of said REED systems may be controlled by the method according to the present invention.

In an embodiment of the method according to the invention, said method further comprises the step of adjusting the concentration and/or flow of said second liquid to the intensity of the applied electric field.

The current reversal is not the only effect, which can introduce deviations in process control. For optimal control of process parameters, it is necessary to control the dialysate concentration and flow as well as temperature and mode of operation. The rate of ion exchange in the REED, which controls the process parameters, depends on a combination of electrical current and passive diffusion. The rate of diffusion depends on the concentration of the ion to be transferred from the dialysate into the reactor. If the dialysate has a high concentration of the pH regulating ion, e.g. hydroxide when operating through an AX-REED, there will be a substantial diffusion of hydroxide into the reactor circuit regardless of the electrical current. It is therefore important to be able to control the concentration of the dialysate so that the rate of diffusion in the REED system alone never exceeds the ion exchange needed for process parameter control. This is done by linking the concentration and/or flow rate of dialysate to the electrical current output to the REED stacks so an increase in current will cause the concentration of dialysate to increase. Control of dialysate concentration can e.g. be carried out be regulating addition of water and concentrated dialysate solution into the dialysate stream prior to its entry in the REED system. Control of dialysate flow can e.g. be carried out by regulating the dialysate flow pump or using flow regulation valves.

It is possible to operate the dialysate flow for a REED system in single pass mode, in batch mode, or a combination hereof depending on the production rate in the bioreactor. If low capacity is required, e.g. in the beginning of a fermentation process where the cell density is low, it is advantageous to circulate the dialysate over a tank. As productivity of the bioreactor increases an increasing percentage of the dialysate leaving the REED stack is discarded. When the process is running at full capacity all dialysate is discarded after a single pass through the stack and fresh dialysate is pumped into the stack. The advantages of operating the dialysate flow in the described fashion encompass improved utilisation of dialysate solution with regard to water and concentrated dialysate solution and improved process parameter control, especially for bioreactor systems, which undergoes significant changes in separation need during a typical process.

If multiple stacks are used it is possible to set up the dialysate flow either in parallel, or in serial mode with or without booster pumps between stacks, in a similar fashion as with the process solution.

In an embodiment of the invention said liquid composition is a fermentation mixture comprising immobilised or suspended microbial cultures or is an enzyme-containing mixture.

In an embodiment of the invention said microbial cultures comprise growing or resting cultures of bacteria, yeast, fungi or mammalian cells.

Another embodiment of the invention is a system for process parameter control of a liquid composition, said system comprising at least a first Reverse Electro-Enhanced Dialysis (REED) membrane stack and a second REED membrane stack, each stack having:
  i) at least two ion-exchange membranes defining a first chamber for a first liquid there between;
  ii) at least two further chambers for a second liquid, each further chamber being located adjacent to the at least one first chamber;
  iii) a set of end membranes; and
  iv) means for applying an electric field over each membrane stack by means of at least two electrodes;
  v) means for reversing the direction of the electric field within any one membrane stack.

In an embodiment of said system said means for reversal of the direction of the electric field applied comprise a voltage regulator adapted to reverse the polarity of said electric field. Means for reversal of the direction of the electric field comprise i.a. one or more relay functions or one or more regulated power supplies.

Another embodiment of the invention is the use of the above system for process parameter control of a liquid composition.

For a bioreactor fermenting by an organic acid-inhibited cell strain, an Anion-Exchange REED (AX-REED) serves to replace produced organic acids with hydroxide ions, and thus, countering the reduction of pH from the acid-formation. By regulation of the AX-REED, the hydroxide exchange can maintain bioreactor pH without the need for neutraliser addition.

Similarly, for a bioreactor fermenting by a base-producing cell strain, a Cation-Exchange REED (CX-REED) serves to replace produced bases with hydrogen ions, countering the increase of pH from the base-formation. As with the AX-REED, by regulation of the CX-REED, the hydrogen exchange can maintain bioreactor pH without the need for neutraliser addition.

In an embodiment of the invention a combination of multiple AX-REED stacks and CX-REED stacks are used, wherein the method according to the invention of asynchronical reversal of the direction of the electric field within any first and second either AX-REED or CX-REED stack is performed. The use of a combination of AX-REED of CX-REED is disclosed in more detail in Applicant's copending patent application entitled "Process for controlling the pH and level of target ions of a liquid composition" of same date, which patent application is hereby incorporated by reference. Said setup allows an optimal control of pH and level of target ions.

The invention will now be described in further details in the following non-limiting specific examples.

EXAMPLES

Example 1

Multiple stacks with asynchronical current reversal intervals for improved pH stability Lactic Acid Bacteria (LAB) fermentations were carried out in a bioreactor connected to an AX-REED system through tubes. Fermentation broth was circulated continuously between the bioreactor and the AX-REED system. The AX-REED was used for control of the pH process parameter of the bioreactor through exchanging the lactate ions (from lactic acid produced in the bioreactor) with hydroxide ions, which maintained a pH close to optimal growing conditions; pH 6.0. The ion-exchange was in turn regulated by a PID control unit, which adjusted the electrical DC current output between the REED electrodes to match the growing production speed of lactic acid, which increased during the trials as the LAB culture grew in numbers simultaneously.

In the first trial, a fed-batch LAB fermentation with 7 liter living broth was connected to a single membrane stack (EUR6 modified to REED, Eurodia SA, France) in an AX-REED system. The stack held 7 cell pairs; each cell pair constituted a compartment for the fermentation broth (sheet flow spacer, Eurodia) and a compartment for an alkaline dialysate (sheet flow spacer, Eurodia), separated by anion-exchange membranes (Neosepta AXE-01, Tokuyama Corp, Japan). Each cell pair had an active membrane area of 560 $cm^2$ for a total of 0.392 $m^2$ active membrane area (560 $cm^2$ per liter broth) for the entire stack.

0.5M NaOH solution was used for the dialysate solution.

The current reversal interval was set to 16 min., meaning that the polarity of each electrode changed every 16th minutes.

After an initial growth period for the LAB culture, the REED system was activated and took over control of bioreactor pH, which was measured by a pH probe inside the stirred bioreactor.

Whenever a current reversal occurred, a short period followed where the REED stack reestablished the ion-exchange process, and in this period, pH dropped in the bioreactor until the REED system again asserted control of the process parameter and regulated the bioreactor pH back to its optimal value. A 30 min. interval of the development of bioreactor pH in this trial is shown in FIG. 1 (single stack).

In a second trial, a fed-batch LAB fermentation with 200 liter living broth was connected to four parallel membrane stacks in an AX-REED system. The stacks were of the same type as was used in the previous trial (EUR6 modified to REED, Eurodia SA, France) and had the same setup, except each stack held 50 cell pairs. The AX-REED system held a total of 11.2 $m^2$ active membrane area (560 $cm^2$ per liter broth).

The trial was carried out with the same general experimental conditions, except that the current reversal interval for each stack was set to 400 seconds. The current reversals were furthermore dispersed asyncronically at regular dispersal intervals of equal length, 100 seconds, in order to reduce the impact on the controlled process parameter, namely the bioreactor pH.

Since both trials were carried out under similar conditions with regard to relative membrane area per ferment broth volume, lactic acid production, separation capacity, and so forth, the development of process parameter, bioreactor pH, has been compared in FIG. 1.

FIG. 1 demonstrates the typical fluctuations in process parameter control for a REED, which occur in connection with a current reversal. For the single stack trial, the fluctuations deviate significantly more from the setpoint, compared to the similar setup with multiple stacks operated with dispersed, asyncronical current reversal intervals. For the single stack, no other effect helps to stabilize the pH fluctuations until the current reversal transition has passed and process parameter control is reassessed to bring back the pH to its setpoint. For multiple stacks, the operating stacks immediately respond to the impact of one stack going into current reversal and increase their effect while the single stack recovers. Even though the multiple stacks offer a significantly higher frequence of process parameter fluctuations, the deviations are significantly lower, which is preferable, especially when operating with microbial process liquids or continuous process solutions.

The invention claimed is:

1. A method for producing a liquid composition, the method comprising at least one step of passing a liquid in a bioreactor or live fermentation process through a first Reverse Electro-Enhanced Dialysis (REED) membrane stack and a second REED membrane stack, each stack having:
   i) at least two ion-exchange membranes defining a first chamber for a first liquid there between;
   ii) at least two further chambers for a second liquid, each further chamber being located adjacent to the at least one first chamber;
   iii) a set of end membranes;
   iv) means for applying an electric field over each membrane stack by means of at least two electrodes;
   v) means for reversing the direction of the electric field within said membrane stacks;
   wherein within one stack, all membranes separating two chambers are of a first ionic type,
   wherein said end membranes are of an ionic type identical to or different from said first ionic type,
   wherein the direction of the electric field within said first membrane stack is reversed at asynchronical intervals of time relative to the reversal of the electric field within said second membrane stack, and wherein said REED membrane stacks are operated in parallel, and
   wherein the process parameters of the liquid in the bioreactor or live fermentation process are controlled by extracting inhibitors like organic acid ions to improve productivity and longevity of cell growth and/or to regulate metabolite production.

2. The method according to claim 1, wherein said process parameters are selected among pH, concentration of target ions and/or conductivity of said liquid composition.

3. The method according to claim 1, wherein the liquid is passed through at least one further REED membrane stack.

4. The method according to claim 3, wherein said at least one further REED membrane stack is an Anion Exchange Reverse Electro-Enhanced Dialysis (AX-REED) membrane stack.

5. The method according to claim 3, wherein said at least one further REED membrane stack is a Cation Exchange Reverse Electro-Enhanced Dialysis (CX-REED) membrane stack.

6. The method according to claim 1, wherein said REED membrane stacks are Anion Exchange Reverse Electro-Enhanced Dialysis (AX-REED) membrane stacks.

7. The method according to claim 1, wherein said REED membrane stacks are Cation Exchange Reverse Electro-Enhanced Dialysis (CX-REED) membrane stacks.

8. The method according to claim 1, wherein the direction of the electric field within any first membrane stack is reversed at substantially regular dispersal intervals relative to the reversals for any second or further membrane stack.

9. The method according to claim 1, wherein the direction of the electric field within any first membrane stack is reversed at dispersal intervals of substantially even length relative to the reversals for any second or further membrane stack.

10. The method according to claim 1, wherein the intensity of the applied electric field is adjusted in response to the pH, concentration of target ions and/or conductivity of said liquid composition.

11. The method according to claim 1, further comprising the step of adjusting the concentration and/or flow of said second liquid to the intensity of the applied electric field.

12. The method according to claim 1, wherein the liquid is a fermentation mixture comprising immobilized or suspended microbial cultures or is an enzyme-containing mixture.

13. The method according to claim 12, wherein said microbial cultures comprise growing or resting cultures of bacteria, yeast, fungi or mammalian cells.

14. A liquid produced by the method according to claim 1.

15. A method for producing a liquid composition, the method comprising the steps of
   a) providing a fermentation mixture comprising a suspended microbial culture;
   b) fermenting said fermentation mixture in a bioreactor;
   c) passing the fermentation mixture through a first Reverse Electro-Enhanced Dialysis (REED) membrane stack and a second REED membrane stack, each stack having:

i) at least two ion-exchange membranes defining a first chamber for a first liquid there between;
   ii) at least two further chambers for a second liquid, each further chamber being located adjacent to the at least one first chamber;
   iii) a set of end membranes;
   iv) means for applying an electric field over each membrane stack by means of at least two electrodes;
   v) means for reversing the direction of the electric field within said membrane stacks;
   wherein within one stack, all membranes separating two chambers are of a first ionic type,
   wherein said end membranes are of an ionic type identical to or different from said first ionic type,
   wherein the direction of the electric field within said first membrane stack is reversed at asynchronical intervals of time relative to the reversal of the electric field within said second membrane stack, and wherein said REED membrane stacks are operated in parallel, thereby obtaining the liquid composition.

16. The method according to claim 15, wherein process parameters of the fermentation mixture are controlled by extracting inhibitors like organic acid ions to improve productivity and longevity of cell growth and/or to regulate metabolite production.

17. A liquid produced by the method according to claim 15.

18. A method for producing a liquid composition, the method comprising the steps of
   a) providing a fermentation mixture comprising a suspended growing yeast culture;
   b) fermenting said fermentation mixture in a bioreactor;
   c) passing the fermentation mixture through a first Reverse Electro-Enhanced Dialysis (REED) membrane stack and a second REED membrane stack, each stack having:
      i) at least two ion-exchange membranes defining a first chamber for a first liquid there between;
      ii) at least two further chambers for a second liquid, each further chamber being located adjacent to the at least one first chamber;
      iii) a set of end membranes;
      iv) means for applying an electric field over each membrane stack by means of at least two electrodes;
      v) means for reversing the direction of the electric field within said membrane stacks;
   wherein within one stack, all membranes separating two chambers are of a first ionic type,
   wherein said end membranes are of an ionic type identical to or different from said first ionic type,
   wherein the direction of the electric field within said first membrane stack is reversed at asynchronical intervals of time relative to the reversal of the electric field within said second membrane stack, and wherein said REED membrane stacks are operated in parallel, thereby obtaining the liquid composition.

19. The method according to claim 18, wherein process parameters of the fermentation mixture are controlled by extracting inhibitors like organic acid ions to improve productivity and longevity of yeast growth and/or to regulate metabolite production.

20. A liquid produced by the method according to claim 18.

* * * * *